US005156761A

United States Patent [19]

Aaslyng et al.

[11] Patent Number: 5,156,761

[45] Date of Patent: Oct. 20, 1992

[54] METHOD OF STABILIZING AN ENZYMATIC LIQUID DETERGENT COMPOSITION

[76] Inventors: Dorrit Aaslyng, Fyrren 8, DK-4000 Roskilde, Denmark; Jadwiga Palicka, Ekbackevaegen 26, S-181 Lidingoe, Denmark, 46

[21] Appl. No.: 666,554

[22] Filed: Mar. 7, 1991

Related U.S. Application Data

[63] Continuation of Ser. No. 354,538, May 19, 1989.

[30] Foreign Application Priority Data

| | | | |
|---|---|---|---|
| Jul. 20, 1988 | [DK] | Denmark | 4039/88 |
| Sep. 21, 1988 | [DK] | Denmark | 5254/88 |
| Oct. 10, 1988 | [DK] | Denmark | 5996/88 |

[51] Int. Cl.[5] ........ C11D 3/386; C11D 7/42; C12N 9/00

[52] U.S. Cl. ........ 252/174.12; 252/DIG. 7; 252/547; 252/526; 252/DIG. 12; 435/264; 435/188

[58] Field of Search ........ 252/174.12, DIG. 12, 252/DIG. 7, 546, 527; 435/264, 188

[56] References Cited

U.S. PATENT DOCUMENTS

| | | | |
|---|---|---|---|
| 3,634,266 | 1/1972 | Thiele et al. | 252/132 |
| 3,655,570 | 4/1972 | Isono et al. | 252/132 |
| 3,707,505 | 12/1972 | Maeda et al. | 252/136 |
| 3,840,480 | 10/1974 | Barrat et al. | 252/545 |
| 4,142,999 | 3/1979 | Bloching et al. | 252/544 |
| 4,261,868 | 4/1981 | Hora et al. | 252/529 |
| 4,287,082 | 9/1981 | Tolfo et al. | 252/174.12 |
| 4,435,307 | 3/1984 | Barbesgaard et al. | 252/174.12 |
| 4,507,219 | 3/1985 | Hughes | 252/118 |
| 4,532,064 | 7/1985 | Boskamp | 252/105 |
| 4,670,179 | 6/1987 | Inamorato et al. | 252/174 |
| 4,769,169 | 9/1988 | Fishlock-Lomax | 252/106 |
| 4,769,173 | 9/1988 | Cornelissen et al. | 252/174.12 |
| 4,931,215 | 6/1990 | Palicka | 252/546 |
| 4,946,136 | 8/1990 | Fishlock-Lomax | 252/546 |

FOREIGN PATENT DOCUMENTS

| | | |
|---|---|---|
| 0160507 | 11/1985 | European Pat. Off. . |
| 0162600 | 11/1985 | European Pat. Off. . |
| 0214868 | 3/1987 | European Pat. Off. . |
| 3640799 | 6/1987 | Fed. Rep. of Germany . |
| 58-021498 | 2/1983 | Japan . |
| 60-123599 | 7/1985 | Japan . |
| 60-123600 | 7/1985 | Japan . |
| 710705 | 6/1954 | United Kingdom . |
| 1277479 | 6/1972 | United Kingdom . |

OTHER PUBLICATIONS

"Ampholak QTE" brochure, from Amphoterics International Lmtd., Jun. 1984.

*Primary Examiner*—Paul Lieberman
*Assistant Examiner*—Kery A. Fries
*Attorney, Agent, or Firm*—Steve T. Zelson; Elias J. Lambiris

[57] ABSTRACT

This invention relates to stabilized enzymatic liquid detergent compositions useful in cleaning a wide range of items including hard surfaces and soft goods such as textiles both for commercial and home use. The stabilization of the enzyme is obtained via the addition of a surfactant composition.

19 Claims, No Drawings

METHOD OF STABILIZING AN ENZYMATIC LIQUID DETERGENT COMPOSITION

This is a continuation application of co-pending application Ser. No. 07/354,538, filed on May 19, 1989.

FIELD OF THE INVENTION

This invention relates to stabilized enzymatic liquid detergent compositions useful in cleaning a wide range of items including hard surfaces and soft goods such as textiles both for commercial and home use.

BACKGROUND OF THE INVENTION

It is well known to formulate aqueous liquid detergents with enzymes. The enzymes incorporated in liquid detergents have mostly been Bacillus proteases, it has also been suggested that incorporation of enzymes other than Bacillus proteases may be useful, e.g. other enzyme types (such as amylases, lipases and cellulases) as well as enzymes of non-Bacillus origin (e.g. fungal enzymes). However, a major problem which has been encountered with such compositions is ensuring sufficient storage stability of the enzymes in such compositions.

Solving the problem of stabilization of enzymes in liquid detergents has been applied in a variety of ways. It is suggested that a number of commonly used detergent ingredients which may reduce storage stability, e.g. anionic surfactants and detergent builders be removed from the detergent composition. It is known that some enzyme stability is generally reduced by the incorporation of a detergent builder. It has also been suggested that various materials that are not detergent-active can be incorporated as enzyme stabilizers.

It is, therefore, an object of this invention to provide a liquid enzymatic detergent composition having improved storage stability.

SUMMARY OF THE INVENTION

The invention disclosed herein is a stabilized enzymatic aqueous liquid detergent composition comprising: (a) an effective amount of an enzyme, (preferably a microbial enzyme) (b) from about 1 to about 50% by weight of an amphoteric surfactant having the general formula (I)

$$R-(A)_n-[\underset{\displaystyle B}{\underset{|}{N}}-(CHR1)_x]_y-N\begin{matrix}\diagup Q\\ \diagdown B\end{matrix} \qquad (I)$$

wherein R is $C_7$–$C_{22}$ alkyl group, optionally substituted by hydroxyl or carboxyl.

A is (CO) or ($OCH_2CH_2$)
n is 0 or 1
R1 is H or $C_1$–$C_6$ alkyl
X is 2 or 3
y is 0 to 4
Q is ($CH_2CH_2OH$) or (R2COOM) where
R2 is $C_1$–$C_6$ alkylene and M is selected from the group consisting of H, an alkali metal, alkaline earth metal, ammonium or substituted ammonium; B is H or a group Q as defined above and (c) a liquid carrier.

Particulary preferred compounds of formula (I) have the structure of formula (II)

$$R-(\underset{\displaystyle CH_2COONa}{\underset{|}{N}}-CH_2CH_2CH_2)_y-N-(CH_2COONa)_2 \qquad (II)$$

wherein R is defined as above and y is 2 or 3.

In formula (II), R is preferably saturated, unbranched and unsubstituted $C_8$–$C_{20}$ Preferred examples of the group R are those derived from coco acids (primarily $C_{12}$–$C_{14}$) and from tallow acids (primarily $C_{16}$–$C_{18}$).

Without wishing to be bound by any theory or mechanism, it is believed that enzyme stabilization is obtained via incorporation of an amphoteric surfactant that is itself detergent active. Thus, the incorporation of non-active material solely for the purpose of enzyme stabilization can be avoided or reduced

DETAILED DESCRIPTION OF THE INVENTION

Microbial Enzymes

The enzyme of this invention is preferably a microbial enzyme. Those enzymes suitable for the present compositions include proteases, lipases, amylases and cellulases. The enzymes are preferably derived from microbial sources, such as Bacillus and fungi. Set forth below are some specific examples of detergent enzymes which are useful in the practice of this invention, each identified by enzyme type, microbial source and reference to a commercial product and/or a patent publication describing the enzyme:

Protease of Bacillus. preferably from *B. licheniformis* (e.g. Alcalase TM) and alkalophilic Bacillus strains according to U.S. Pat. No. 3,723,250 (e.g. Savinase TM and Esperase TM) (commercially available from Novo Industri A/S).

Alpha-amylase of Bacillus, preferably *B. licheniformis.* (Termamyl TM, commercially available from Novo Industri A/S).

Protease of Fusarium, preferably *F. oxysporum* U.S. Pat. No. 3,652,399 (Takeda); or Protease Fusarium, according to co-pending PCT application PCT/DK 89/0001, filed Jan. 6, 1989.

Cellulase of Humicola preferably *H. insolens.* (e.g., celluzyme TM) (commercially available from Novo Industri A/S), U.S. Pat. No. 4,435,307 (Novo).

Lipase of Humicola, preferably *H. lanuginosa.* (Lipolase TM) (commercially available from Novo Industri A/S),EP 305,216 and U.S. Pat. No. 4,810,414 (Novo).

The detergent of the invention may contain two or more detergent enzymes. Preferred formulations include combinations of any two of the above enzymes, particularly combinations of a Bacillus protease and any one of the other above enzymes.

A preferred amount of active enzyme present in an enzyme product would be about 0.01–5% of the product. This would result in the enzyme protein comprising about 0.0002%–0.3% of the detergent composition.

Amphoteric Surfactant of Formula (I)

Commercially available examples of amphoteric surfactant having the general formula (I) include Deriphat 151 TM, Deriphat 154 TM, Deriphat 151C TM, Deriphat 161C TM (products available from Henkel), Amphoram CPl TM, Diamphoram CPl TM, Triamphoram CPl TM, and Polyamphoram TM (products available from Ceca), and Ampholak 7TX TM and Ampholak XC0-30 TM (products available from Berol Nobel AB). The formulas of the two latter products are preferred for use with this invention as follows:

Ampholak 7TX ™

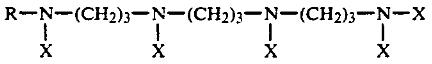

R = $C_{16-18}$

X = $-CH_2-COONa$

Ampholak XC0-30 ™

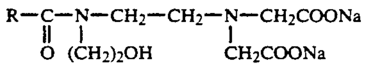

Other Surfactants

The detergent composition of the invention will preferably also contain from about 3 to about 20% by weight of a nonionic surfactant. Further, the composition may optionally contain from about 3 to about 15% by weight of an anionic surfactant and/or a second amphoteric surfactant. It may be preferable that the composition is essentially free of anionic surfactant, as this may destabilize some enzymes.

Examples of suitable surfactants in the practice of this invention are:

Nonionics: Nonyl phenol ethoxylate and alcohol ethoxylate.

Anionics: linear alkylbenzene sulfonate, secondary alkane sulfonate, alcohol ethoxylate sulfate and alpha olefin sulfonate.

2nd amphoteric: Iminodipropionate (e.g. Ampholak YCE TM, commercially available from Berol Nobel AB, Sweden), and iminopropionate.

Other Ingredients

The liquid detergent of the invention may be aqueous (i.e., in an aqueous based carrier),preferably containing from about 20% to about 70% of water and about 0 to about 20% of an organic solvent (i.e., in a mixed aqueous/organic carrier), or containing from about 1 to about 20% of water and from about 5 to about 25% of solvent. Satisfactory enzyme stability may be obtained even at water contents about 50%. Alternatively, the liquid detergent composition may be essentially free of water (e.g. water content below 1%), and in that formulation will preferably comprise 10-30% of solvent (i.e., primarily in an organic carrier).

Preferred organic solvents are mono- and divalent lower alcohols and glycol ethers.

The detergent composition of the invention may be built (i.e. comprising a detergent builder) or unbuilt (i.e. essentially free of a detergent builder). Enzyme stability is generally better in an unbuilt composition, but it may be desirable to include a builder for improved detergency. Builders are components which perform a number of functions. They remove metal ions like calcium and magnesium from the washing solution, from soil and from fibers. These are eliminated by builders in a soluble form by sequestration or in an insoluble form by precipitation. Builders enhance the cleaning effectiveness of the surfactants. They maintain the alkalinity in the wash solution, increase the negative zeta potentials of soil and fabric and thus aid in preventing certain soils from redeposition during the washing process. A built composition preferably contains about 1-40%, by weight of a builder such as zeolite, phosphate, phosphonate, citrate, NTA, EDTA or DTPA.

A soluble calcium salt is also preferably included in the liquid detergent in an amount of about 1-20 millimoles Ca per liter, as calcium stabilizes many detergent enzymes.

The pH will typically be neutral or alkaline. A particularly preferred pH is between 8-10.

The compositions may also contain, depending on the intended use, additives such as fabric condition (e.g. quaternary ammonium salt, preferably 1-5%), foam boosters (preferably 1-5%), bactericides (preferably 1-5%), optical brighteners (preferably 0.1-1%), dyes (preferably 0.1-1%) and perfumes (preferably 0.1-1%).

EXAMPLE

Samples of essentially unbuilt (B and BI), zeolite-built (ZI) and citrate built (C) liquid detergents with various water content were prepared with the following general composition (% by weight, as active material, as shown in Table 1):

TABLE 1

| Detergent | B | BI | ZI | C |
|---|---|---|---|---|
| Water | 54.9% | 64.9% | 65.6% | 65.1% |
| Triethanolamine | 10.0 | 8.0 | 2.8 | 3.7 |
| Fatty acid ($C_{12}$-$C_{14}$) | | 7.0 | 5.6 | |
| Ethanol | 5.0 | 4.0 | | |
| Polyacrylate | | 0.7 | 3.0 | |
| Propylene glycol | | 5.0 | 3.0 | 0.7 |
| Zeolite S | | | 18.9 | |
| Phosphonate | 2.0 | 1.6 | | 1.0 |
| $CaCl_2.2H_2O$ | 0.1 | 0.1 | 0.1 | |
| Citric acid | | | | 5.0 |
| NaOH | | | | 2.4 |
| Diethyleneglycol monoethylether | | | | 3.0 |
| Nonionic surfactant | 10.0 | 8.0 | 7.0 | 12.0 |
| Anionic/amphoteric surfactant | 6.0 | 4.8 | 4.2 | 4.8 |
| | 100% | 100% | 100% | 100% |

ph. adjusted to 9.0

The polyacrylate was Alcosperse 409 TM, and the phosponate was Dequest 2006 TM. The non-ionic surfactant was alcohol ethoxylate and consisted of the following Dobanol TM types:(Shell): 25-9, 23-6.5 and 23-3 in the ratio 3:1:1, and for detergent C it consisted of Dobanol 23-6.5 only. The anionic/amphoteric surfactant in each formulation as set forth in Table 1 above was one of the following:

1. LAS (anionic), linear alkylbenzene sulfonate, Sulfosoft TM (Berol)
2. SAS (anionic), secondary alkane sulfonate, Hostapur SAS 60 TM (Hoechst)
3. AES (anionic), alcohol ethoxylate sulfate, Dobanol 25-3S TM (Shell)
4. AOS (anionic), alpha olefin sulfonate (Ethyl corp.)
5. Ampholak 7TX TM (amphoteric of this invention)
6. 7TX (amphoteric) +LAS (anionic) ratio 2:1
7. Ampholak XC0-30 TM (amphoteric of this invention)
8. 7TX+Ampholak YCE TM (2nd amphoteric), in the ratio 3:1

One of the following enzymes was added to each detergent sample:

1% of Savinase 8.0L TM (alkalophilic)

1.5% of Celluzyme TM (Humicola cellulase)

0.5% of Lipolase TM (fungal lipase) (% by weight of commercial enzyme preparation relative to the detergent)

The samples were stored at 37 degrees C. for two weeks, the enzyme activity was measured before and after storage, and the results were expressed as residual activity in % of initial activity.

TABLE 2

| | % residual activity | | | | | | | |
|---|---|---|---|---|---|---|---|---|
| | 1 LAS | 2 SAS | 3 AES | 4 AOS | 5 7TX | 6 LAS + 7TX | 7 XCO − 30 | 8 7TX + YCE |
| Detergent B | | | | | | | | |
| Savinase | 60.0 | 67.0 | 71.0 | 70.0 | 91.0 | 61.0 | | |
| Alcalase | 5.0 | | 15.0 | | 21.0 | 22.0 | | |
| Esperase | 60.0 | | 66.0 | | 86.0 | | | |
| Celluzyme | 45.0 | 47.0 | 55.0 | 56.0 | 80.0 | 67.0 | | |
| Lipolase | 53.0 | | | | 79.0 | | | |
| Detergent BI: | | | | | | | | |
| Alcalase | 6.0 | | | | 31.0 | | | |
| Savinase | 36.0 | 40.0 | 45.0 | 45.0 | 83.0 | 81.0 | 51.0 | 51.0 |
| Celluzyme | 52.0 | 59.0 | 51.0 | 63.0 | 73.0 | 66.0 | 97.0 | 74.0 |
| Detergent ZI: | | | | | | | | |
| Savinase | 9.0 | 2.0 | 5.0 | 6.0 | 26.0 | 21.0 | 26.0 | 29.0 |
| Detergent C: | | | | | | | | |
| Alcalase | 7.0 | | | | 22.0 | | | |
| Savinase | 10.0 | | | | 63.0 | | | |
| Esperase | 32.0 | | | | 49.0 | | | |
| Celluzyme | 24.0 | | | | 57.0 | | | |

For all formulations tried, it is seen that complete substitution (columns 5 and 7) and partial substitution (columns 6 and 8) of anionic with amphoteric surfactant according to the disclosure herein improves the storage stability of the enzyme.

The present invention is not to be limited in scope by the above example since they are intended as illustration of the invention. Indeed, various modifications of the invention in to those shown and described herein will become apparent to those skilled in the art from the foregoing description. Such modifications are intended to fall within the scope of the appended claims.

We claim:

1. A method of stabilizing an enzymatic liquid detergent composition comprising:

providing an amphoteric surfactant of formula (I)

$$R-[\underset{\substack{|\\B}}{N}-(CHR^1)_x]_y-\underset{\substack{|\\B}}{N}-Q \qquad (I)$$

wherein

R is $C_7$–$C_{22}$ alkyl group, optionally substituted by hydroxyl or carboxyl;

$R^1$ is H or $C_1$–$C_6$ alkyl;

x is 2 or 3;

y is 2 or 3;

Q is ($R^2COOM$);

B is H or ($R^2COOM$) where $R^2$ is $C_1$–$C_6$ alkylene; and

M is selected from the group consisting of H, an alkali metal metal, alkaline earth metal, ammonium or substituted ammonium;

to a liquid detergent composition comprising a cleaning effective amount of an enzyme and a liquid carrier, wherein said amphoteric surfactant is present in an amount of from about 1 to about 50% by weight of said liquid determined composition.

2. The method according to claim 1, wherein said amphoteric surfactant has the formula (II):

$$R-(\underset{\substack{|\\CH_2COONa}}{N}-CH_2CH_2CH_2)_y-N-(CH_2COONa)_2 \qquad (II)$$

wherein R is a $C_7$–$C_{22}$ alkyl group, optionally substituted by hydroxyl or carboxyl and y is 2 or 3.

3. The method according to claim 1, wherein said enzyme is a microbial enzyme.

4. The method according to claim 3, wherein said microbial enzyme is a Bacillus enzyme.

5. The method according to claim 4, wherein said Bacillus enzyme is a protease or an amylase.

6. The method according to claim 1, wherein said enzyme is a fungal detergent enzyme.

7. The method according to claim 6, wherein said fungal detergent enzyme is a protease, lipase or cellulase.

8. The method according to claim 6, wherein said enzyme is selected from the group consisting of a Fusarium protease, a Humicola lipase and a Humicola cellulase.

9. The method according to claim 1, wherein said liquid detergent composition further comprises an cleaning cleaning effective amount of a second microbial enzyme.

10. The method according to claim 1, wherein said amphoteric surfactant is present in an amount of from about 3 to 40% by weight of said liquid detergent composition.

11. The method according to claim 1, wherein said liquid detergent composition further contains about 1 to 20% by weight of a nonionic surfactant.

12. The method according to claim 1, wherein said liquid detergent composition further contains about 1 to 20% by weight of an anionic surfactant.

13. The method according to claim 1, wherein said liquid detergent composition further contains about 1 to 20% by weight of a second amphoteric surfactant.

14. The method according to claim 1, wherein said liquid carrier is water and an organic solvent.

15. The method according to claim 1, wherein said liquid detergent composition is about 20 to 70% by weight of water and 0 to about 20% by weight of a solvent.

16. The method according to claim 1, wherein said liquid carrier is an organic solvent.

17. The method according to claim 16, wherein said liquid detergent composition is about 10 to 30% by weight of said organic solvent.

18. The method according to claim 1, wherein said liquid detergent composition further comprises about 1 to 40% by weight of a detergent builder.

19. The method according to claim 1, wherein said liquid detergent composition further comprises about 1 to 20 millimoles per liter of a soluble calcium salt.

* * * * *